(12) United States Patent
Masui et al.

(10) Patent No.: US 10,168,289 B2
(45) Date of Patent: Jan. 1, 2019

(54) METHOD FOR EVALUATING CROSSLINK CONCENTRATION IN CROSSLINKED RUBBER

(71) Applicant: SUMITOMO RUBBER INDUSTRIES, LTD., Kobe-shi, Hyogo (JP)

(72) Inventors: Tomomi Masui, Kobe (JP); Hiroyuki Kishimoto, Kobe (JP)

(73) Assignee: SUMITOMO RUBBER INDUSTRIES, LTD., Kobe-shi, Hyogo (JP)

(*) Notice: Subject to any disclaimer, the term of this patent is extended or adjusted under 35 U.S.C. 154(b) by 127 days.

(21) Appl. No.: 15/142,002

(22) Filed: Apr. 29, 2016

(65) Prior Publication Data

US 2016/0349196 A1 Dec. 1, 2016

(30) Foreign Application Priority Data

May 27, 2015 (JP) ................................ 2015-107642

(51) Int. Cl.
*G01N 23/20* (2018.01)
*G01N 23/202* (2006.01)
*G01N 23/201* (2018.01)
*G01N 33/44* (2006.01)
*C08F 212/08* (2006.01)

(52) U.S. Cl.
CPC ......... *G01N 23/202* (2013.01); *C08F 212/08* (2013.01); *G01N 23/201* (2013.01); *G01N 33/445* (2013.01); *G01N 2223/054* (2013.01); *G01N 2223/106* (2013.01); *G01N 2223/1016* (2013.01); *G01N 2223/345* (2013.01)

(58) Field of Classification Search
CPC .. G01N 23/201; G01N 23/202; G01N 33/445; C08J 3/24; C08L 19/003
See application file for complete search history.

(56) References Cited

U.S. PATENT DOCUMENTS

| | | | | |
|---|---|---|---|---|
| 9,851,342 B2 * | 12/2017 | Kaneko | ............... | G01N 33/445 |
| 2013/0324311 A1 * | 12/2013 | Mashita | ............. | A63B 37/0051 |
| | | | | 473/372 |
| 2015/0376394 A1 * | 12/2015 | Veraart | ................. | C08F 279/02 |
| | | | | 524/504 |

FOREIGN PATENT DOCUMENTS

| | | |
|---|---|---|
| JP | 2001-261891 A | 9/2001 |
| JP | 2007-153209 A | 6/2007 |
| JP | 2010-78523 A | 4/2010 |

OTHER PUBLICATIONS

M. Takenaka, "Structure analyses of crosslinked rubber by small angle neutron scattering", Nippon Gomu Kyokaishi, No. 7, 2014, 4 pages.*

Ikeda et al., "Vulcanization: New Focus on a Traditional Technology by Small-Angle Neutron Scattering," Macromolecules, vol. 42, No. 7, 2009, pp. 2741-2748.

* cited by examiner

*Primary Examiner* — Michael C Bryant
(74) *Attorney, Agent, or Firm* — Birch, Stewart, Kolasch & Birch, LLP

(57) ABSTRACT

A method for evaluating the crosslink concentration in a crosslinked rubber is provided. The present invention relates to a method for evaluating the crosslink concentration in a crosslinked rubber by small-angle X-ray scattering or small-angle neutron scattering using measurement samples prepared by swelling the crosslinked rubber to different degrees of swelling.

1 Claim, 2 Drawing Sheets

METHOD FOR EVALUATING CROSSLINK CONCENTRATION IN CROSSLINKED RUBBER

TECHNICAL FIELD

The present invention relates to a method for evaluating crosslink concentration in a crosslinked rubber.

BACKGROUND ART

The concentration of crosslinks in gels or rubbers is closely related to their physical properties. Patent Literatures 1 to 3 propose methods for evaluating the concentration of crosslinks in a crosslinked rubber using a test to indicate the crosslink concentration. In this test, a crosslinked rubber is swollen in toluene, which is a good solvent for the polymer in a crosslinked rubber, and the ratio of the volume of the rubber before and after swelling is used as the degree of swelling to evaluate the crosslink concentration.

Moreover, according to the disclosure of Non-Patent Literature 1, a crosslinked rubber swollen as described above is analyzed by small-angle neutron scattering to evaluate the size of network inhomogeneities which correspond to portions of the swollen crosslinked rubber that have a relatively high crosslink density.

The methods by measuring the degree of swelling as disclosed in Patent Literatures 1 to 3 merely allow for the evaluation of the overall concentration of crosslinks in a crosslinked rubber and cannot be used to determine details of the variation in crosslink concentration, e.g. the crosslink concentration in network inhomogeneities. Moreover, the methods by evaluating the size of network inhomogeneities by small-angle neutron scattering as disclosed in Non-Patent Literature 1 merely evaluate the size of network inhomogeneities in crosslinked rubber materials and cannot be used to determine the crosslink concentration in the network inhomogeneities. Thus, there is a need for a method for evaluating crosslink concentration which is closely related to the physical properties.

CITATION LIST

Patent Literature

Patent Literature 1: JP-A 2001-261891
Patent Literature 2: JP-A 2007-153209
Patent Literature 3: JP-A 2010-78523

Non-Patent Literature

Non-Patent Literature 1: Macromolecules, 2009, 42 (7), pp. 2741-2748

SUMMARY OF INVENTION

Technical Problem

The present invention aims to solve the above problems and provide a method for evaluating crosslink concentration in a crosslinked rubber.

Solution to Problem

The present invention relates to a method for evaluating crosslink concentration in a crosslinked rubber by small-angle X-ray scattering or small-angle neutron scattering using measurement samples prepared by swelling the crosslinked rubber to different degrees of swelling.

Preferably, the method includes measuring two or more swollen crosslinked rubbers with different degrees of swelling in terms of an overall degree of swelling Q, and a size $\Xi$ of polymer network inhomogeneities determined by small-angle X-ray scattering or small-angle neutron scattering; approximating a relationship between the overall degree of swelling Q and the size $\Xi$ of polymer network inhomogeneities by the expression (3) below; and calculating an index $\alpha$ of crosslink concentration in the polymer network inhomogeneities according to the expression (3-1) below to evaluate relative crosslink concentration in the polymer network inhomogeneities:

$$\Xi = \frac{d\Xi}{dQ^{1/3}}(Q^{1/3} - 1) + \Xi_0 \quad \text{Expression (3)}$$

$$\alpha = \frac{1}{\Xi_0} \cdot \frac{d\Xi}{dQ^{1/3}}, \quad \text{Expression (3-1)}$$

wherein $\Xi$: size of polymer network inhomogeneities;
$\alpha$: index of crosslink concentration in polymer network inhomogeneities;
Q: overall degree of swelling of crosslinked rubber; and
$\Xi_0$: size of polymer network inhomogeneities in non-swollen state.

Preferably, the swollen crosslinked rubbers are prepared by placing the crosslinked rubber and an arbitrary amount of a solvent together in a hermetically-sealed container to allow the entire crosslinked rubber to be uniformly swollen.

The present invention relates to a method for evaluating crosslink concentration in a crosslinked rubber by small-angle X-ray scattering or small-angle neutron scattering using measurement samples prepared by swelling the crosslinked rubber to different degrees of swelling, the method including: measuring two or more swollen crosslinked rubbers with different degrees of swelling in terms of an overall degree of swelling Q, and a size $\Xi$ of polymer network inhomogeneities determined by small-angle X-ray scattering or small-angle neutron scattering; approximating a relationship between the overall degree of swelling Q and the size $\Xi$ of polymer network inhomogeneities by the expression (3) below; and calculating an index $\alpha$ of crosslink concentration in the polymer network inhomogeneities according to the expression (3-1) below to evaluate relative crosslink concentration in the polymer network inhomogeneities, wherein the size of polymer network inhomogeneities is determined by fitting the expression (2) below to a scattering intensity curve I(q) obtained by the X-ray scattering or neutron scattering in a region q defined by the expression (1) below:

$$\Xi = \frac{d\Xi}{dQ^{1/3}}(Q^{1/3} - 1) + \Xi_0 \quad \text{Expression (3)}$$

$$\alpha = \frac{1}{\Xi_0} \cdot \frac{d\Xi}{dQ^{1/3}}, \quad \text{Expression (3-1)}$$

wherein $\Xi$: size of polymer network inhomogeneities;
$\alpha$: index of crosslink concentration in polymer network inhomogeneities;
Q: overall degree of swelling of crosslinked rubber; and
$\Xi_0$: size of polymer network inhomogeneities in non-swollen state, $$q = \frac{4\pi \sin(\theta/2)}{\lambda} \qquad \text{Expression (1)}$$

wherein θ: scattering angle; and
λ: wavelength of X-rays or neutrons, $$I(q) = \frac{I_\xi(0)}{1+q^2\xi^2} + \sum_{n=1} \frac{I_\Xi(0)}{(1+q^2\Xi_n^2)^2} \qquad \text{Expression (2)}$$

wherein $I_\xi(0)$, $I_\Xi(0)$, $\xi$, and $\Xi_n$ indicate fitting parameters; q indicates the region defined by the expression (1); and $\Xi_n < \Xi_{n+1}$.

Advantageous Effects of Invention

Since the evaluation method of the present invention involves small-angle X-ray scattering or small-angle neutron scattering using measurement samples prepared by swelling a crosslinked rubber to different degrees of swelling, it enables evaluation of crosslink concentration in the crosslinked rubber. In particular, the method makes it possible to evaluate relative crosslink concentration in the polymer network inhomogeneities present in the crosslinked rubber by using a relation between the overall degrees of swelling and the sizes of polymer network inhomogeneities determined by small-angle X-ray scattering or small-angle neutron scattering of two or more swollen crosslinked rubbers with different degrees of swelling.

DESCRIPTION OF EMBODIMENTS

Figure 1A:
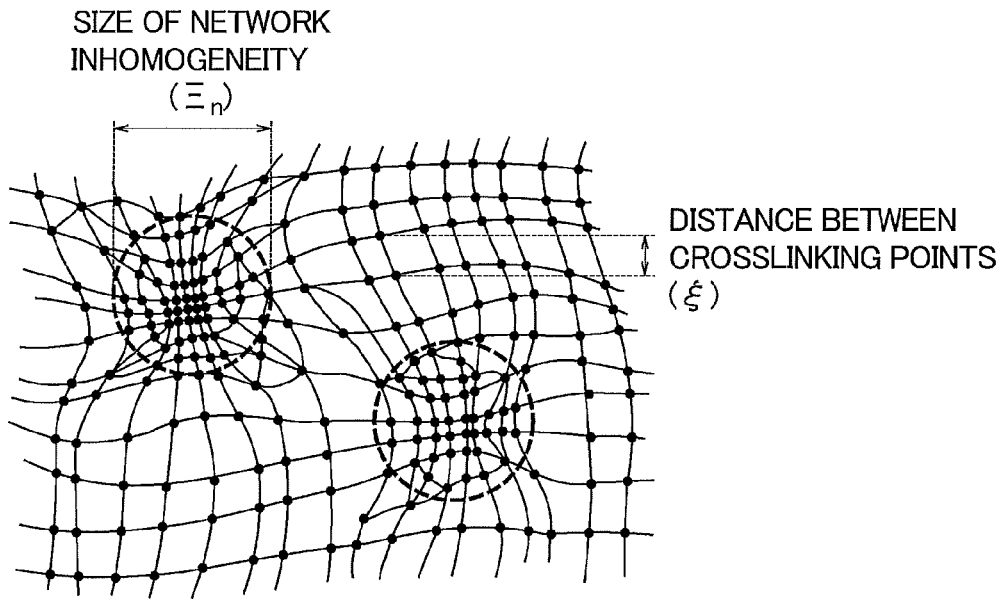
FIGS. 1 (a) and (b) are schematic views showing crosslink concentrations in swollen crosslinked rubbers.

The present invention involves evaluation of crosslink concentration in a crosslinked rubber by small-angle X-ray scattering or small-angle neutron scattering using measurement samples prepared by swelling the crosslinked rubber to different degrees of swelling. The swollen crosslinked rubbers with different degrees of swelling can be prepared, for example, by varying the amount of a solvent added to the crosslinked rubber.

In conventional methods for evaluating crosslink concentration in a crosslinked rubber, the crosslinked rubber is completely swollen in an excess amount of a solvent or the like, and then the degree of swelling (hereinafter also referred to as "full degree of swelling") of the crosslinked rubber is measured and used to analyze the overall concentration of crosslinks in the crosslinked rubber, or to analyze the relative overall concentration of crosslinks in the crosslinked rubber by comparison with the full degree of swelling of another crosslinked rubber. With these methods, it is difficult to analyze differences in crosslink concentration between crosslinked rubbers.

As a result of extensive studies, the present inventors have found that crosslink concentration in a crosslinked rubber can be evaluated by small-angle X-ray scattering or small-angle neutron scattering using measurement samples prepared by swelling a single crosslinked rubber to different degrees of swelling. The present invention has been completed based on the above finding.

The present inventors have found particularly that the relative crosslink concentration in the polymer network inhomogeneities present in a single crosslinked rubber can be evaluated by measuring two or more swollen crosslinked rubbers with different degrees of swelling in terms of the overall degree of swelling Q, and the size Ξ of polymer network inhomogeneities determined by small-angle X-ray scattering or small-angle neutron scattering to obtain a relationship between the overall degree of swelling Q and the size Ξ of polymer network inhomogeneities, more preferably by linearly approximating the relationship to determine the slope, or still more preferably by approximating the relationship by the expression (3) below and calculating an index α of crosslink concentration in the polymer network inhomogeneities according to the expression (3-1) below.

Crosslinked rubbers need to be swollen in the measurement of crosslink concentration in the crosslinked rubbers by small-angle X-ray scattering or small-angle neutron scattering. In other words, crosslinked rubbers need to be swollen to more easily determine the concentration of crosslinks in the crosslinked rubbers. However, it is difficult to equalize the degrees of swelling of crosslinked rubbers having different degrees of crosslinking. Thus, it has been difficult to compare the crosslink concentrations of different crosslinked rubbers which differ in degree of swelling. The present inventors have found that the relative crosslink concentration in the polymer network inhomogeneities present in a crosslinked rubber can also be evaluated comparatively with that of a different crosslinked rubber by the technique of the present invention, and particularly by measuring two or more swollen crosslinked rubbers with different degrees of swelling in terms of the overall degree of swelling Q, and the size Ξ of polymer network inhomogeneities determined by small-angle X-ray scattering or small-angle neutron scattering to obtain a relationship between the overall degree of swelling Q and the size Ξ of polymer network inhomogeneities, more preferably by linearly approximating the relationship to determine the slope, or still more preferably by approximating the relationship by the expression (3) below and calculating an index α of crosslink concentration in the polymer network inhomogeneities according to the expression (3-1) below.

The term "polymer network inhomogeneity" as used herein, which will be described in detail later, refers to a structural portion of a crosslinked rubber that has a high crosslink density as shown in FIG. 1(a).

$$\Xi = \frac{d\Xi}{dQ^{1/3}}(Q^{1/3}-1) + \Xi_0 \qquad \text{Expression (3)}$$

$$\alpha = \frac{1}{\Xi_0} \cdot \frac{d\Xi}{dQ^{1/3}}, \qquad \text{Expression (3-1)}$$

(Ξ: size of polymer network inhomogeneities;
α: index of crosslink concentration in polymer network inhomogeneities;

Q: overall degree of swelling of crosslinked rubber;
Ξ$_0$: size of polymer network inhomogeneities in non-swollen state)

In the present invention, crosslink concentration in a crosslinked rubber can be evaluated by use of small-angle X-ray scattering (hereinafter also referred to as SAXS analysis) that measures scattering intensity by irradiating a crosslinked rubber with X-rays (scattering angle: usually 10 degrees or less). In the small-angle X-ray scattering, structural information of a substance can be obtained by measuring the X-rays scattered at small scattering angles among the scattered X-rays resulting from the irradiation of the substance with X-rays. Based on the information, inhomogeneities on the order of a few nanometers, such as microphase-separated structures, in crosslinked rubbers can be analyzed.

In the present invention, crosslink concentration in a crosslinked rubber can also be evaluated by use of small-angle neutron scattering (hereinafter also referred to as SANS analysis) that measures scattering intensity by irradiating a crosslinked rubber with neutrons (scattering angle: usually 10 degrees or less). In the small-angle neutron scattering, structural information of a substance can be obtained by measuring the neutrons scattered at small scattering angles among the scattered neutrons resulting from the irradiation of the substance with neutrons. Based on the information, inhomogeneities on the order of a few nanometers, such as microphase-separated structures, in crosslinked rubbers can be analyzed.

The brilliance and number of photons of X-rays in the SAXS analysis, the flux density of neutrons in the SANS analysis, the measurement methods, the measurement apparatuses and the like may suitably be as described in JP-A 2014-102210 (which is incorporated by reference in its entirety) and the like. Although the SANS analysis is superior in terms of contrast, the SAXS analysis is preferred because it is versatile and allows the effects of the present invention to be well achieved.

The SAXS or SANS analysis is carried out in a region q defined by the expression (1) below.

$$q = \frac{4\pi \sin(\theta/2)}{\lambda} \qquad \text{Expression (1)}$$

(θ: scattering angle; λ: wavelength of X-rays or neutrons)

The X-rays scattered in the SAXS measurement are detected by an X-ray detector, and an image is then generated by an image processor or the like using the X-ray detection data from the X-ray detector.

Examples of the X-ray detector include two-dimensional detectors such as X-ray films, nuclear emulsion plates, X-ray image pickup tubes, X-ray fluorescent amplifiers, X-ray image intensifiers, X-ray imaging plates, X-ray CCDs, and X-ray amorphous materials, and line sensor one-dimensional detectors. The X-ray detector may be appropriately selected according to the type and the conditions of a polymer material to be analyzed, and the like.

The image processor may appropriately be an ordinary one that can generate X-ray scattering images based on X-ray detection data from an X-ray detector.

The SANS analysis can also be carried out based on the same principle as in the SAXS analysis; the neutrons scattered are detected by a neutron detector, and an image is then generated by an image processor or the like using the neutron detection data from the neutron detector. Similarly as above, the neutron detector may be a known two-dimensional detector or one-dimensional detector, and the image processor may be a known one that can generate neutron scattering images. These devices may be appropriately selected.

Any crosslinked rubber may be used in the present invention as long as it is a crosslinked rubber obtained by cross-linking a rubber component including natural rubber, styrene-butadiene rubber or the like by a vulcanizing agent commonly used in in the field of rubber industry, such as sulfur and a vulcanization accelerator. The crosslinked rubber may contain other compounding agents generally used in the field of rubber industry, including, for example, reinforcing agents such as silica and carbon black, silane coupling agents, zinc oxide, stearic acid, various antioxidants, oils, waxes, and crosslinking agents. Such a crosslinked rubber can be prepared using a known kneading method and the like.

In the present invention, a crosslinked rubber is swollen to different degrees of swelling to prepare measurement samples to be used. Specifically, a single crosslinked rubber to be evaluated for concentration of crosslinks is swollen to two or more degrees of swelling to prepare measurement samples to be used. The use of the measurement samples prepared by swelling a crosslinked rubber to different degrees of swelling enables the crosslinked rubber to be evaluated for crosslink concentration.

In the method of the present invention, it is preferred to swell a crosslinked rubber to three or more different degrees of swelling in order to evaluate crosslink concentration more precisely.

The term "swollen crosslinked rubbers with different degrees of swelling" as used herein refer to two or more swollen crosslinked rubbers having different degrees of swelling, prepared from a single crosslinked rubber. The term "degree of swelling" is defined as follows: ((volume of crosslinked rubber)+(volume of a compound used in swelling))/(volume of crosslinked rubber). The term "volume of a compound (solvent) used in swelling" refers to the volume of a compound (solvent) accumulated in the crosslinked rubber. For example, in the case of a crosslinked rubber having a volume of 100 mm$^3$ in which the full degree of swelling is 4 as determined by completely swelling the crosslinked rubber in an excess amount of toluene added thereto, swollen crosslinked rubbers with degrees of swelling of 2 and 3 prepared by adding 100 mm$^3$ and 200 mm$^3$ of toluene, respectively, may be used, or swollen crosslinked rubbers with degrees of swelling of 2 and 4 prepared by adding 100 mm$^3$ and 300 mm$^3$ of toluene, respectively, may be used.

As for the method for swelling a crosslinked rubber, any known method can be used as long as the crosslinked rubber can be swollen. Methods using solvents such as toluene can be suitably used. The swelling conditions are not particularly limited as long as they allow the crosslinked rubber to be uniformly swollen. Yet, it is preferred to place the crosslinked rubber and an arbitrary amount of a solvent together in a hermetically-sealed container to allow the entire crosslinked rubber to be uniformly swollen. To allow the crosslinked rubber to be uniformly swollen means that a solvent or the like used in swelling is evenly distributed in the crosslinked rubber so as not to result in the crosslinked rubber having warpage or the like due to an uneven distribution of the solvent in the crosslinked rubber.

Generally, warpage occurs in a crosslinked rubber when the crosslinked rubber is swollen in a solvent or the like. Such warpage indicates that the solvent or the like has not been evenly distributed in the crosslinked rubber. By placing the crosslinked rubber and the solvent together for preferably at least 6 hours, more preferably at least 12 hours, still more preferably at least 24 hours, the solvent or the like can be evenly distributed in the crosslinked rubber and the warpage can also be eliminated, whereby the entire crosslinked rubber can be uniformly swollen.

Figure 1B:
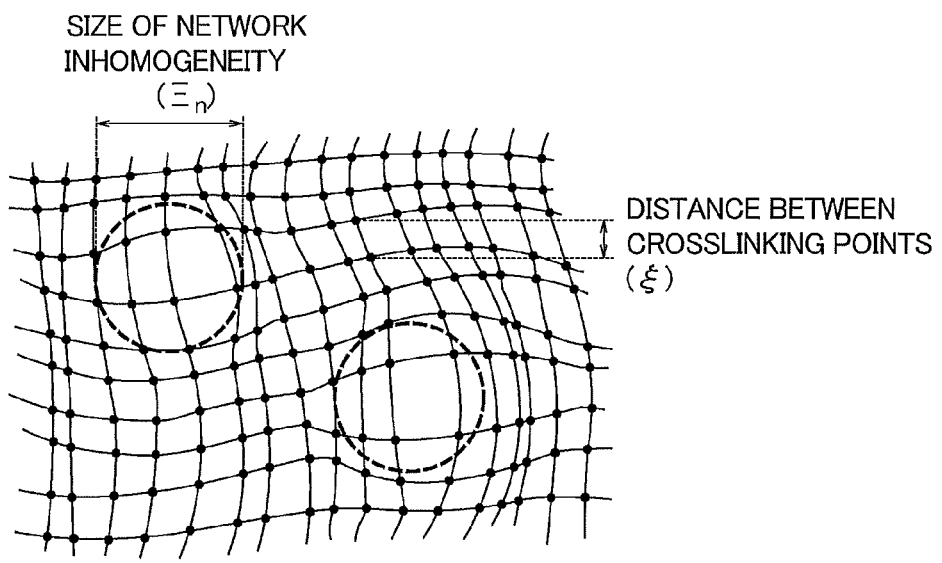

Each swollen crosslinked rubber with a different degree of swelling is subjected to SAXS or SANS analysis to prepare a scattering intensity curve, which is then analyzed as described below to determine the structure size of scatterers (polymer network inhomogeneities) each having a correlation length $\Xi_n$. The term "polymer network inhomogeneity" as used herein refers to a structural portion of a crosslinked rubber that has a high crosslink density as shown in FIG. 1(a), among the schematic structures showing crosslink concentrations in crosslinked rubbers as shown in FIG. 1, and the term is not intended to include structural portions having low crosslink densities as shown in FIG. 1(b). Yet, the method of the present invention is applicable to both structural portions having high crosslink densities and structural portions having low crosslink densities.

The structural portions having high crosslink densities and the structural portions having low crosslink densities can be distinguished from each other by comparing the crosslink concentration index numbers (a lower crosslink concentration index $\alpha$ indicates a denser crosslink concentration).

Figure 2:
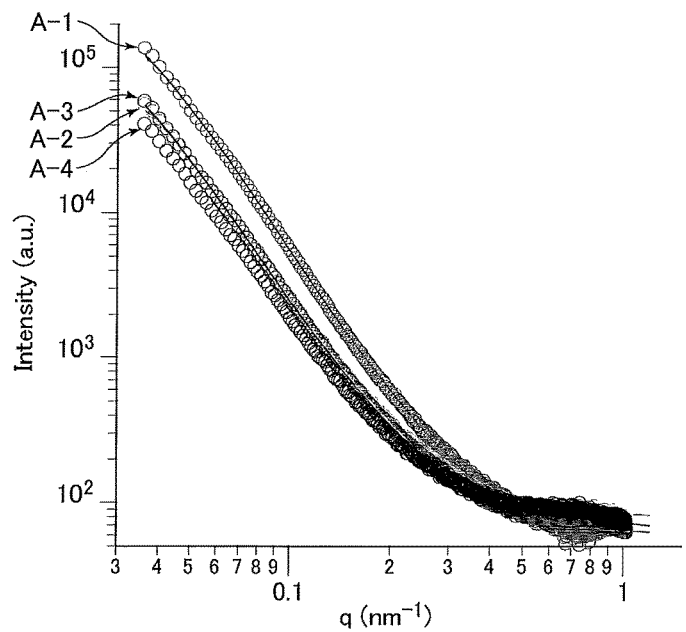
FIG. 2 shows examples of scattering intensity curves of crosslinked rubber samples A-1 to A-4 obtained by small-angle X-ray scattering.

The scattering intensity curve I(q) obtained by SAXS or SANS analysis as shown in FIG. 2 is fitted to the expression (2) below to determine the fitting parameters by least squares.

$$I(q) = \frac{I_\xi(0)}{1+q^2\xi^2} + \sum_{n=1} \frac{I_\Xi(0)}{(1+q^2\Xi_n^2)^2} \qquad \text{Expression (2)}$$

In the above expression, $I_{86}(0)$, $I_\Xi(0)$, $\xi$, and $\Xi_n$ indicate fitting parameters; q indicates the region defined by the expression (1); and $\Xi_n < \Xi_{n+1}$.

In the expression (2), among the fitting parameters determined, a correlation length $\xi$ of 1 nm to 10 nm is assumed to correspond to the distance between crosslinking points in the polymer, and a correlation length $\Xi_n$ of 10 nm to 100 µm is assumed to correspond to the size of network inhomogeneities in the polymer.

In this way, as described above, the structure size of scatterers each having the correlation length $\Xi_n$ corresponding to the network inhomogeneities in the polymer is determined. The structure size of scatterers each having the correlation length $\Xi_n$ corresponds to the size of polymer network inhomogeneities.

The scattering intensity curve I(q) obtained by SAXS or SANS analysis as shown in FIG. 2 may be fitted with the expressions (5-1) and (5-2) below to determine the fitting parameters by least squares.

In this case, among the fitting parameters, a radius of gyration $R_{gi}$ of 1 to 10 nm is assumed to correspond to the distance between crosslinking points in the polymer, and a radius of gyration $R_{gi}$ of 10 nm to 100 µm is assumed to correspond to the size of network inhomogeneities in the polymer.

$$I_{(q)} = \sum_{i=1}^{n}\left\{P_i\left[\left\{erf\left(\frac{qR_{gi}}{\sqrt{6}}\right)^3 / q\right\}\right]^{D_{fi}} \exp\left(\frac{-q^2 R_{g(i+1)}^2}{3}\right) + \right. \qquad \text{Expression (5-1)}$$

$$\left. G_i \exp\left(\frac{-q^2 R_{g(i+1)}^2}{3}\right)\right\} +$$

$$P_{n+1}\left[\left\{erf\left(\frac{qR_{g(n+1)}}{\sqrt{6}}\right)^3 / q\right\}\right]^{D_{f(n+1)}}$$

$$erf(z) = \frac{2}{\sqrt{\pi}} \int_0^z e^{-t^2} dt \qquad \text{Expression (5-2)}$$

($P_i$, $G_i$, $R_{gi}$, $D_{fi}$: fitting parameters;
n: integer;
q: as defined above;
z, t: arbitrary positive numbers)

As described above, each swollen crosslinked rubber with a different degree of swelling is subjected to SAXS or SANS analysis to prepare a scattering intensity curve, which is then analyzed by the above method using the expression (2) or the like to determine the structure size of scatterers (polymer network inhomogeneities) each having a correlation length $\Xi_n$, i.e. the size $\Xi$ of polymer network inhomogeneities.

Next, each swollen crosslinked rubber subjected to SAXS or SANS analysis is measured for the degree of swelling.

Then, the relative crosslink concentration in the polymer network inhomogeneities present in the crosslinked rubber can be evaluated by using a relationship between the overall degree of swelling Q and the size $\Xi$ of network inhomogeneities, measured on two or more swollen crosslinked rubbers with different degrees of swelling, more preferably by linearly approximating the relationship to determine the slope, or still more preferably by approximating the relationship by the expression (3) below and calculating an index $\alpha$ of crosslink concentration in the polymer network inhomogeneities according to the expression (3-1) below.

The method of linear approximation or the method of approximation using the expression (3) below is not particularly limited. Methods using least squares or the like may be used.

$$\Xi = \frac{d\Xi}{dQ^{1/3}}(Q^{1/3}-1) + \Xi_0 \qquad \text{Expression (3)}$$

$$\alpha = \frac{1}{\Xi_0} \cdot \frac{d\Xi}{dQ^{1/3}}, \qquad \text{Expression (3-1)}$$

($\Xi$: size of polymer network inhomogeneities;
$\alpha$: index of crosslink concentration in polymer network inhomogeneities;
Q: overall degree of swelling of crosslinked rubber;
$\Xi_0$: size of polymer network inhomogeneities in non-swollen state)

As for the swelling percentage calculated by the expression below, the difference (b−a) between the swelling percentage "a" of a swollen crosslinked rubber with the lowest degree of swelling and the swelling percentage "b" of a swollen crosslinked rubber with the highest degree of swelling, among two or more swollen crosslinked rubbers with different degrees of swelling, is preferably 10 or more, more preferably 25 or more, still more preferably 30 or more. Moreover, the upper limit of the difference (b−a) is not particularly limited, but is preferably 95 or less. When the difference is in the range described above, a more precise evaluation of crosslink concentration can be achieved.

$$\text{Swelling percentage (\%)} = ((\text{degree of swelling of crosslinked rubber})-1)/((\text{full degree of swelling of crosslinked rubber})-1) \times 100$$

In the above description, the index α of crosslink concentration in the polymer network inhomogeneities present in the crosslinked rubber is calculated assuming that the polymer network inhomogeneities contained in the crosslinked rubber have the same size. In the case where the polymer network inhomogeneities contained in the crosslinked rubber do not have the same size, for example, swollen crosslinked rubbers with different degrees of swelling may be prepared from the same crosslinked rubber piece to allow the same network inhomogeneities to be measured for changes in their size, or measurement samples may be altered as appropriate, for example. In such a manner, any treatment to allow the network inhomogeneities to be measured for the amount of size change may be used.

The ratio ($d\Xi/dQ^{1/3}$) of the amount of change in the size of network inhomogeneities to the amount of change in the degree of swelling can be calculated using the expression (3). Further, in the equation (3-1), the value of $d\Xi/dQ^{1/3}$ can be divided by the size $\Xi_0$ of polymer network inhomogeneities in the non-swollen state (calculated using the expression (3)) to calculate an index α that allows network inhomogeneities having different $\Xi_0$ values to be comparatively evaluated for crosslink concentration.

A lower index α of crosslink concentration calculated using the expression (3-1) indicates that the ratio of the amount of change in the size of network inhomogeneities to the amount of change in the degree of swelling is lower, and the amount of the compound used in swelling and accumulated in the network inhomogeneities is smaller and, therefore, the crosslink density is higher. This means that it is possible to determine relative crosslink concentration in terms of how much the crosslink density of the network inhomogeneities is higher than that of other portions. In addition, it is also possible to evaluate different crosslinked rubbers for relative crosslink concentration in terms of how much the crosslink density of the network inhomogeneities in a crosslinked rubber is higher than that of another crosslinked rubber. Consequently, by the measurement of crosslink concentration, which is highly associated with the physical properties of crosslinked rubbers, a causal relationship between crosslink concentration and rubber physical properties can be determined in detail, which is expected to provide guiding principles for control of crosslinking, thereby making a great contribution in the development of rubber compositions.

Furthermore, in the present invention, the size $\Xi_0$ of polymer network inhomogeneities in the non-swollen state can be calculated using the expression (3). Thus, the size of polymer network inhomogeneities in the non-swollen state can be determined for various crosslinked rubbers. This allows for the quantification of crosslink concentration in the non-swollen state, which has been conventionally difficult, and thus provides guiding principles for structural control, thereby making a great contribution in the development of rubber compositions.

EXAMPLES

The present invention is specifically described with reference to examples, but the present invention is not limited to these examples.

The chemical agents used in examples are listed below.
(Chemical Agents Used)
Toluene: available from Kanto Chemical Co., Inc.
Styrene butadiene rubber (SBR): NS116R available from Zeon Corporation
Sulfur: sulfur powder available from Tsurumi Chemical Industry Co., Ltd.
Vulcanization accelerator: Nocceler NS (N-tert-butyl-2-benzothiazyl sulfenamide) available from Ouchi Shinko Chemical Industrial Co., Ltd.
(Composition of Crosslinked Rubber A and Preparation Method Thereof)

Using the compounding ratio of 100 parts by mass SBR, 2 parts by mass sulfur, and 1 part by mass the vulcanization accelerator, SBR was masticated in an open roll mill, sulfur and the vulcanization accelerator were added, and the mixture was kneaded in an open roll mill. The resulting kneaded mixture was vulcanized at 170° C. for 12 minutes to prepare crosslinked rubber A.
(Composition of Crosslinked Rubber B and Preparation Method Thereof)

Crosslinked rubber B was prepared in the same manner as in the (Composition of crosslinked rubber A and preparation method thereof), except that vulcanization was carried out at 150° C. for 35 minutes.
(Preparation of Completely Swollen Crosslinked Rubber and Measurement of its Degree of Swelling (Full Degree of Swelling))

Test pieces having a size of 10 mm×10 mm×1 mm (length×width×thickness) cut out from the crosslinked rubber A or B were immersed in an excess amount of toluene at room temperature for at least 24 hours, and then the degree of swelling (the amount of change in the volume of each test piece before and after immersion in toluene) was calculated.
(Preparation of Swollen Crosslinked Rubbers with Different Degrees of Swelling)
(Crosslinked Rubber A)

To each test piece having a size of 10 mm×10 mm×1 mm (length×width×thickness) cut out from the crosslinked rubber A was added a volume of 68, 389, 467, or 817 mm³ of toluene with a micropipette at room temperature. These test pieces were hermetically sealed in glass vials and immersed for at least 24 hours, thus obtaining swollen crosslinked rubbers A-1 to A-4 with different degrees of swelling.
(Crosslinked Rubber B)

To each test piece having a size of 10 mm×10 mm×1 mm (length×width×thickness) cut out from the crosslinked rubber B was added a volume of 80, 410, or 575 mm³ of toluene with a micropipette at room temperature. These test pieces were hermetically sealed in glass vials and immersed for at least 24 hours, thus obtaining swollen crosslinked rubbers B-1 to B-3 with different degrees of swelling.

The prepared swollen crosslinked rubbers A-1 to A-4 and B-1 to B-3 were evaluated in terms of swelling percentage, size of network inhomogeneities, and index of crosslink concentration in the network inhomogeneities as follows. Tables 1 and 2 show the results.
(Swelling Percentage)

Swelling percentage was calculated for the swollen crosslinked rubbers A-1 to A-4 and B-1 to B-3 using the following expression.

$$\text{Swelling percentage (\%)} = ((\text{degree of swelling of crosslinked rubber})-1)/((\text{full degree of swelling of crosslinked rubber})-1) \times 100$$

(Measurement of Size of Network Inhomogeneities)

The test pieces of the swollen crosslinked rubbers A-1 to A-4 and B-1 to B-3 were subjected to small-angle X-ray scattering to prepare scattering intensity curves I(q) (FIG. 2 shows examples of A-1 to A-4). These scattering intensity curves I(q) were each fitted to the above expression (2) to determine the size of network inhomogeneities. The apparatuses and measurement conditions used in the small-angle X-ray scattering are described below.

(SAXS Apparatus)
SAXS analysis apparatus provided with the beamline BL08B2 of the large synchrotron radiation facility "SPring-8" belonging to Japan Synchrotron Radiation Research Institute (Measurement Conditions)
Brilliance of X-rays (8 keV): $9.5 \times 10^{15}$ photons/s/mrad$^2$/mm$^2$/0.1% bw
Number of photons of X-rays: $10^9$ to $10^{10}$ photons/s
Distance between sample and detector: 2.58 m (Detector)
High-speed two-dimensional X-ray detector PILATUS 100K
(available from Dectris Ltd.)

(Index of Crosslink Concentration in Network Inhomogeneities)

Figure 3:
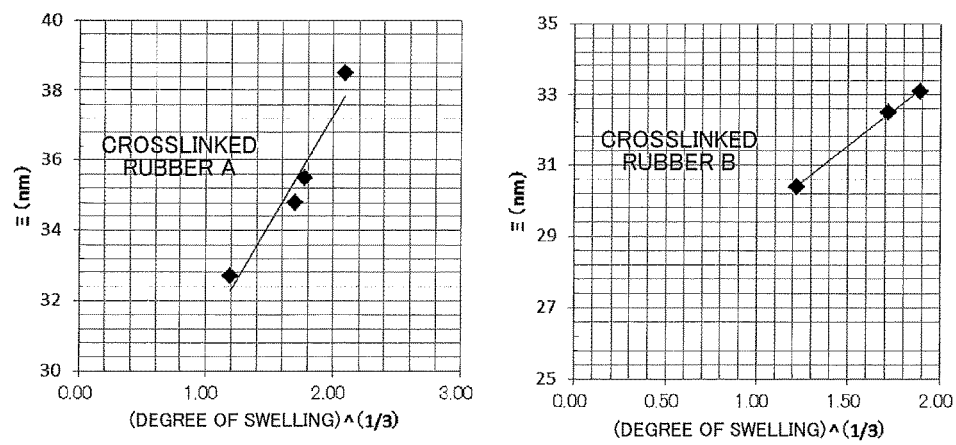
FIG. 3 show relations between the overall degrees of swelling and the sizes of polymer network inhomogeneities of samples of crosslinked rubber A or B, and also show approximate straight lines obtained by approximating the relations by the expression (3).

A relation between the degrees of swelling and the sizes of network inhomogeneities measured on the swollen crosslinked rubbers A-1 to A-4 was approximated by the above expression (3) by least squares (FIG. 3). Then, the size $\Xi_0$ of network inhomogeneities in the non-swollen crosslinked rubber and the ratio $d\Xi/dQ^{1/3}$ were calculated, and an index α of crosslink concentration was calculated using the above expression (3-1). Similarly, also for the swollen crosslinked rubbers B-1 to B-3, the size $\Xi_0$ of network inhomogeneities in the non-swollen crosslinked rubber and the ratio $d\Xi/dQ^{1/3}$ were calculated, and an index α of crosslink concentration was calculated using the above expression (3-1).

TABLE 1

| | Crosslinked rubber A | | | |
|---|---|---|---|---|
| | Swollen crosslinked rubber A-1 | Swollen crosslinked rubber A-2 | Swollen crosslinked rubber A-3 | Swollen crosslinked rubber A-4 |
| Full degree of swelling | | | 9.17 | |
| Degree of swelling Q | 1.68 | 4.89 | 5.67 | 9.17 |
| Swelling percentage (%) | 8 | 48 | 57 | 100 |
| (Degree of swelling Q)^(1/3) | 1.19 | 1.70 | 1.78 | 2.09 |
| Size Ξ (nm) of network inhomogeneities | 32.7 | 34.8 | 35.5 | 38.5 |

| | Crosslinked rubber B | | |
|---|---|---|---|
| | Swollen crosslinked rubber B-1 | Swollen crosslinked rubber B-2 | Swollen crosslinked rubber B-3 |
| Full degree of swelling | | 6.75 | |
| Degree of swelling Q | 1.80 | 5.10 | 6.75 |
| Swelling percentage (%) | 14 | 71 | 100 |
| (Degree of swelling Q)^(1/3) | 1.22 | 1.72 | 1.89 |
| Size Ξ (nm) of network inhomogeneities | 30.4 | 32.5 | 33.1 |

TABLE 2

| | Crosslinked rubber A | Crosslinked rubber B |
|---|---|---|
| Size $\Xi_0$ of network inhomogeneities in non-swollen crosslinked rubber | 31.1 | 29.5 |
| Index α of crosslink concentration in network inhomogeneities | 0.199 | 0.138 |

As shown in Tables 1 and 2, the technique of the present invention enabled evaluation of crosslink concentration in crosslinked rubbers. In particular, the technique revealed relative crosslink concentration in the polymer network inhomogeneities present in the crosslinked rubbers.

The invention claimed is:

1. A method for evaluating crosslink concentration in a crosslinked rubber by small-angle X-ray scattering or small-angle neutron scattering using measurement samples prepared by swelling the crosslinked rubber to different degrees of swelling,
    wherein the swollen crosslinked rubbers are prepared by placing the crosslinked rubber and an arbitrary amount of a solvent together in a hermetically-sealed container to allow the entire crosslinked rubber to be uniformly swollen.

* * * * *